United States Patent [19]

Hartford et al.

[11] 4,407,585

[45] Oct. 4, 1983

[54] SCENT-AWAKE CLOCK

[76] Inventors: Louise D. Hartford, 391 Durant Ave., Staten Island, N.Y. 10308; James P. Kavoussi, 1401 80th St., Brooklyn, N.Y. 11228

[21] Appl. No.: 330,030

[22] Filed: Dec. 11, 1981

[51] Int. Cl.³ .............................................. G04B 47/00
[52] U.S. Cl. .................................... 368/12; 368/72; 368/250
[58] Field of Search ............... 222/70, 645, 646, 647, 222/648; 368/250, 12, 72–75, 243

[56] References Cited

U.S. PATENT DOCUMENTS

| | | | |
|---|---|---|---|
| 3,150,800 | 9/1964 | Weber | 222/647 |
| 3,203,594 | 8/1965 | Jones | 222/647 |
| 3,289,886 | 12/1966 | Goldsholl et al. | 222/648 X |
| 3,455,102 | 7/1969 | Wolf | 368/250 X |
| 3,587,332 | 6/1971 | Bell | 222/645 X |
| 3,632,020 | 1/1972 | Nixon et al. | 222/646 |
| 3,643,836 | 2/1972 | Hunt | 222/648 |
| 3,647,116 | 3/1972 | Nixon et al. | 222/647 |
| 3,952,916 | 4/1976 | Phillips | 222/645 |
| 4,185,283 | 1/1980 | Clark | 368/73 X |

Primary Examiner—Ulysses Weldon
Attorney, Agent, or Firm—Richard L. Miller

[57] ABSTRACT

An alarm clock that awakens a sleeper by the scent of smell. A housing is provided in which is mounted a storage container of aromatic liquid, which liquid is dispensed at a preset time by a timing mechanism. Various dispensing mechanisms are disclosed for releasing the liquid from the container at the preset time. In the first embodiment, the storage container has a spray nozzle, which is pressed downwardly at the preset time and at intervals by a lever arm pivoted by a solenoid operated by the timing mechanism. In another embodiment, the storage container is vacuum sealed, and a U-shaped tube is provided in which a first end is placed outside of the tube and the other end inside the tube above the liquid level. The solenoid operates a pivotal arm that alternately exposes the open end of the tube to air to supply pressure in the container and thus forces out the liquid. In still another form of the invention, the aromatic liquid may be released from its container in response to the operation of a hammer of a conventional buzzer alarm clock.

7 Claims, 5 Drawing Figures

SCENT-AWAKE CLOCK

BACKGROUND OF THE INVENTION

The present invention is directed to an alarm clock to awaken a sleeper from his sleep, or otherwise to give a preset signal.

It is well-known that conventional alarm clocks awaken a sleeper by a buzzer and, in some instances, by a flashing light either used in conjunction with the buzzer or separately. However, a buzzer system can often startle the sleeper, which is dangerous to a person with known heart trouble, and cannot be effective when the sleeper is deaf. Further, the flashing light may be ineffective to a sleeper if he or she is blind or even if he or she is turned away from the light source so that the flashing light does not reach the eyes of the sleeper. Further, flashing lights also can be disturbing to a sleeper.

SUMMARY OF THE INVENTION

It is, therefore, the primary object of the present invention to provide an alarm clock that overcomes the above-noted drawbacks of prior art devices, and which utilizes the sense of smell to awaken a sleeper rather than the sense of hearing and/or the sense of sight.

To this end, the present invention provides for an aromatic liquid to be dispensed at a preset awakening time, which dispensed liquid then evaporates and permeates the air of the room with a pleasant smell.

To achieve this object, the present invention provides a storage container full of an aromatic liquid, which is easily evaporated. Such liquids may be standard perfumes and colognes, readily purchased at stores. In the preferred form of the invention, the liquid is stored in a spray bottle, which has a spray nozzle. A timer is provided which timer activates a solenoid and plunger, which then pivots a lever arm into contact with the nozzle. The lever arm will push down on the spray nozzle, thus forcing the liquid evaporant out of the bottle and through a hole formed in the housing of the device. The sprayed aromatic liquid will evaporate and provide a smell in the room that is pleasant, and thus awaken the sleeper in a gentle and safe manner.

In another embodiment of the invention, the storage bottle may be provided with an outlet that is a hollow needle, with one open end of the needle positioned in the container and the other open end positioned outside of the container. When the lever arm is pivotted downwardly into contact with the container, which is a plastic bag in this embodiment, the liquid is forced out of the container through the hollow needle onto a tray having a layer of absorbent material thereon, such as cotton. A fan blows air over the cotton absorbing layer to thus evaporate the aromatic liquid and direct it through the opening forced in the housing toward the sleeper to awaken him.

In still another embodiment of the invention, the aromatic liquid is released by a U-shaped tube having a first open end outside of the container and a second open end inside the container above the liquid lever. The container is vacuum-packed, so that when the U-shaped tube is allowed to be opened to the ambient air, the air enters inside the container, thus partially alleviating the vacuum, and forcing liquid out through a hollow needle at the bottom thereof. The open end of the U-shaped tube is controlled by a flat plate, which in turn is pivotted to a connecting lever, which itself is pivotted to the lever arm operated by the solenoid.

In all of the above embodiments, the solenoid is activated by a timer of conventional design, which timer may be set to release the aromatic liquid at a preset, alarm-awakening time. Further, a blinker also of standard design is provided which causes the solenoid, and fan when provided, to operate intermittantly.

In still another embodiment of the invention, the liquid storing and dispensing container of the present invention may be used with a conventional big ben type buzzer alarm clock, with the bells thereof removed, so that the hammer may reciprocate freely. In this embodiment, the lever arm which in previous embodiments was operated by a solenoid, is operated by the hammer, which itself is operated by the buzzer alarm system of the clock, in the conventional manner. In this form of the invention, any of the dispensing means may be used in conjunction with the hammer-operated lever arm.

BRIEF DESCRIPTION OF THE DRAWING FIGURES

The invention will be more readily understood with reference to the accompanying drawing, wherein FIG. 1 is a perspective view of the housing for the scent-alarm clock of the present invention, with the timer and opening shown in the front panel thereof;

DETAILED DESCRIPTION OF THE PREFERRED EMBODIMENT

Figure 1:
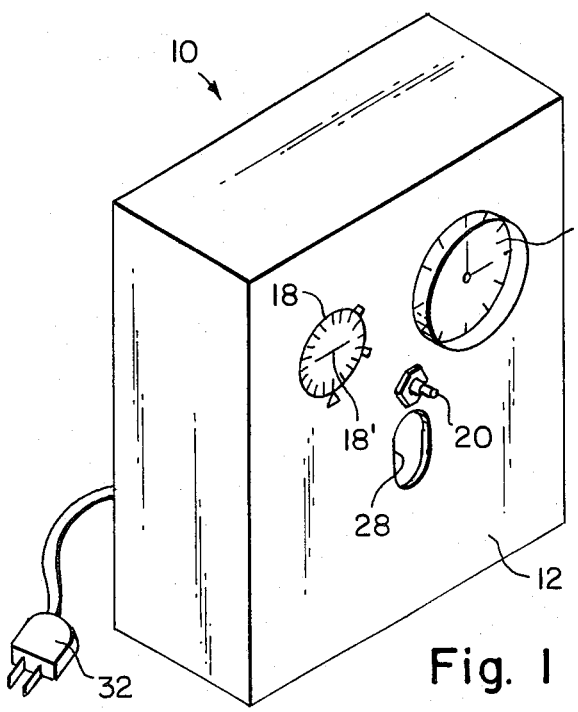
Figure 2:
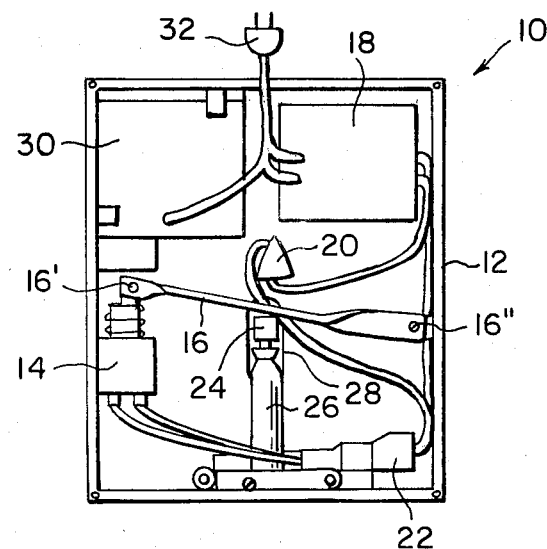
FIG. 2 is an end view of the interior of the housing of the present invention with the rear panel thereof removed to show the parts mounted in the housing.
Figure 3:
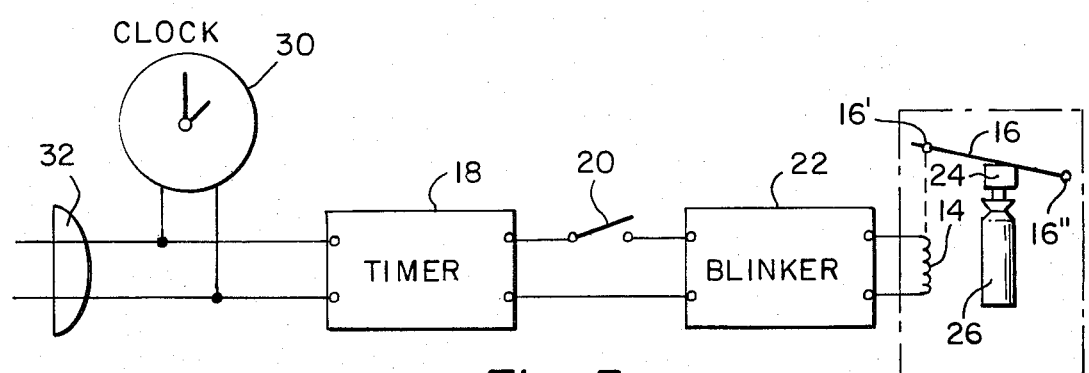
FIG. 3 is an electrical schematic of the control circuitry of the present invention.

Referring now to the drawing, and particularly FIGS. 1 and 2, the scent-awake alarm clock of the present invention is generally indicated by reference numeral 10, and includes a housing 12 in which are mounted the various operating means for creating an aroma by which to awaken a sleeper. The interior of the housing 12 mounts a solenoid 14 with its reciprocal plunger. Pivotally connected to the plunger is a first end 16' of lever arm 16, which is also pivotally connected at its second end 16" to a side wall of the housing, as clearly shown in FIG. 2. The solenoid 14 is activated by a timer 18 of conventional design and well-known in the art, which timer 18 supplies current to the solenoid upon reaching a preset alarm-waking time, which time is set via hand 18'. An on-off plug 20 is connected between the timer 18 and a blinker 22 of conventional design, which blinker supplies current to the solenoid at intermittent intervals, so that the solenoid plunger is reciprocated, and thus the lever arm 16 is also reciprocated about its pivot end 16".

Upon reaching the preset alarm-waking time, the solenoid will reciprocate the lever arm 16 such that a spray nozzle 24 at the top of a container or bottle 26, in which is stored the aromatic liquid, is actuated in an up-and-down fashion, so that the spray of aromatic liquid is dispensed from the bottle 26. An opening 28 is formed in the front panel of the housing, as shown in FIG. 1, which opening is provided adjacent the spray nozzle 24, so that the spray of aromatic liquid exits through the opening. The spray upon exiting will quickly evaporate and create a scent in the room in which it is provided, thus awakening a sleeper by the sense of smell rather than by the sense of hearing, as is the custom.

The housing 12 is also provided with a standard alarm clock 30 which awakens a sleeper with the usual buzzer sound via a hammer acting on bells. This alarm clock 30 may be used in conjunction with the scent alarm clock of the present invention for hard-to awaken sleepers, or for a change of routine. A male plug 32 supplies the power to both timer 18 and alarm clock 30.

Figure 4:
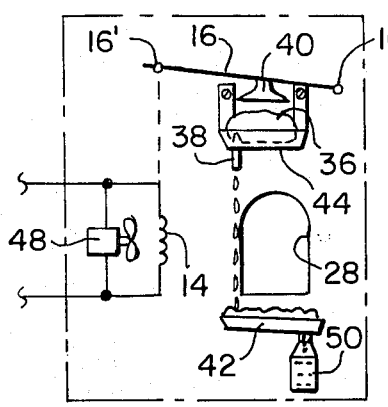
FIG. 4 is a schematic of the second embodiment of the present invention where the scent is achieved by removal from a squeezable plastic bag storing the aromatic liquid.

In FIG. 4, a second embodiment of the invention is shown. In this embodiment, instead of supplying the scent via a spray nozzle, the container storing the aromatic liquid is in the form of a squeezable plastic bag 36. The bottom of the plastic bag 36 is provided with an outlet 38, which outlet is in the form of a hollow needle having a first open end within the plastic bag to a position adjacent the bottom surface of the plastic bag. A second opening of the hollow needle lies outside of the plastic bag, so that when pressure is created within the plastic bag by means of a plunger 40 attached to the lever arm 16, the liquid will exit via the hollow needle and drop onto a tray 42, which tray 42 is mounted directly below the outlet 38. The plastic bag 36 is mounted within the housing on a support 44, which support also mounts the hollow needle 38. Preferably, the tray 42 is provided with an absorbent material, such as cotton, which will hold the aromatic liquid while a fan 48 blows air thereover to evaporate the liquid and create a scent within the room. The fan is preferably positioned so that it directs its stream of air toward the opening 28 in the front panel of the housing, through which the evaporated liquid is passed. The lever arm 16 is operable in the same manner as that shown in the first embodiment. The fan in this embodiment is intermittent as is the solenoid, so that the wind supplied thereby is provided only upon the dropping of aromatic liquid on the tray. A storage receptacle 50 may also be provided for the tray 42, which receptacle receives excess liquid evaporant, so that it may be used again. An opening in the tray allows for the receptacle to fit snugly therein with its open top and extending in the opening to receive the excess liquid.

Figure 5:
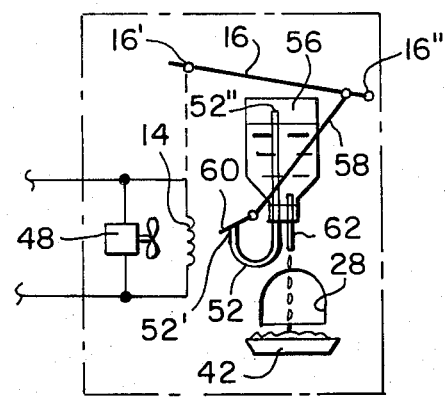
FIG. 5 is a schematic of another embodiment of the present invention where the scent is achieved by gradually eliminating a vacuum in the storage container for the aromatic liquid.

In FIG. 5, another embodiment of the invention is shown in which the storage container or bottle full of aromatic liquid is vacuum packed with a U-shaped hollow tube 52 provided. The hollow tube 52 has a first open end 52' outside of the storage bottle and at a level below the cap of the bottle which is mounted upside down in the housing. The hollow tube has a second open end 52" inside the bottle and extends upwardly above the liquid surface to the vacuum space 56. A connecting lever arm 58 is pivotally connected at one end thereof to the lever arm 16, and at its other end is pivotally connected to a connecting lever or flat plate 60. The flat plate 60 alternately covers and exposes the first opening 52' of the hollow tube 52, so that when the opening is exposed to the ambient air, air pressure is provided in the hollow interior of the bottle, thus creating only a partial vacuum in the storage container. The pressure in the bottle thus forces the liquid downwardly and through the outlet 62, which is a hollow needle similar to the hollow needle 38 of FIG. 4. As can be seen in FIG. 5, the flat plate slides along the face of the opening 52' by movement of the connecting lever 58, which itself is moved in an up-and-down fashion by the lever arm 16, as in the other embodiments described above.

Though the fan 48 may be operated only at the same intervals as the operation of the solenoid 14, it is also possible to continually operate the fan so that a sleeper will be aided in awakening by the breeze provided by the fan impinging of the sleeper's face.

It is noted that the levers 58 and 60 may be used to operate a ball seal in a storage bottle, instead of operating on the U-tube 52. In this case, the lever or flat plate 60 is supported upon a horizontal rest support, and has its remote end upturned, so that as the connecting lever 58 is moved downwardly in response to the activation of the solenoid, the flat plate 60 will be moved along the horizontal rest support. The end of the rest support is positioned adjacent the ball seal of the storage bottle, and the end of this rest support is also upturned, so that as the flat plate slides along the surface of the horizontal rest support, the upturned end of the rest support will cause the flat plate to pivot slightly upwardly relative to the end of the connecting arm to which the flat plate is attached, so that the upturned end of the flat plate will strike the ball seal and move it upwardly, and thereby open the bottle to allow the liquid therein to drip outwardly and downwardly to a tray situated therebelow. A fan may also be provided in this embodiment to speed up the evaporation of the liquid absorbed in the cotton absorbing layer of the tray.

In still another embodiment of the invention, the ball seal storage container may be combined with a storage receiving bottle, instead of a receiving tray, with the liquid dripping from the ball seal container mounted above the opening to the receiving storage container mounted directly below it. In this embodiment, the storage bottle is opened and closed at its top opening by a lever arrangement with flat plate similar to the one shown in FIG. 5. In this embodiment, there are two connecting lever arms 58, the first connecting the lever arm 16 with the upturned flat plate on the rest support tray to operate the ball seal, and the other arm 58 connecting the lever arm 16 to the flat plate which opens and closes the storage container in the manner shown in FIG. 5. Thus, both flat plates are simultaneously operated to open and close their respective storage containers at the same time so that when the top container is opened to drip liquid downwardly, the lower receiving container is opened to receive the liquid. That portion of the falling liquid evaporant that is actually evaporated by a fan or the like, in the manner as described above, will exit through the opening in the housing to provide a scent to a sleeper to awaken him. However, that portion of the falling liquid that is not evaporated will fall into the receiving bottle for storage therein and subsequent use.

The present invention may also be utilized in combination with a conventional "big ben" type buzzer alarm clock. In this embodiment, the bells of the alarm clock are removed, so that the hammer thereof is allowed to reciprocate freely. Then, the lever arm 16 is attached to the hammer, so that when the preset time is reached to awaken the sleeper, the hammer will cause the up-and-down movement of the lever arm 16, instead of a solenoid with plunger. The types of scent-applying mechanisms as shown and described above may be used with this form, with the only difference being that the lever arm 16 is activated by the hammer of the alarm clock rather than by the solenoid. Further, the storage bottle and outlet means for the bottle, may all be mounted on the exterior housing of the buzzer alarm clock, with a tray also provided to catch the released liquid evaporant.

While specific embodiments of the invention have been shown and described, it is to be understood that numerous changes and modifications may be made therein without departing from the scope and spirit of the invention, as set out in the appended claims.

What is claimed is:

1. A scent-awake clock for awakening a sleeper through the sense of smell comprising a housing; aromatic means in said housing for giving off a scent when dispensed; means for storing and dispensing said aromatic means in said housing; actuating means operably connected to said means for storing and dispensing, said actuating means selectively causing said aromatic means to be dispensed form said means for storing and dispensing; and timing means for activating said actuating means at a predetermined time, said aromatic means comprising a liquid stored in said means for storing and dispensing said means for storing and dispensing comprising a container, said actuating means comprising a solenoid electrically connected to said means for activating, and a lever arm pivoted at one end thereof to said housing, the other end of said lever arm being connected to the plunger of said solenoid for movement thereby, said lever arm operating said means for storing and dispensing said aromatic means to thereby dispense said aromatic means, wherein said lever arm comprises a plunger means located between said one end and said other end thereof, said plunger means extending downwardly from said lever arm towards said container; said container comprising a sealed liquid-filled squeezable bag which is alternately squeezed and expanded by said plunger means to cause said aromatic means to exit therefrom, said squeezable bag having outlet means at the bottom thereof through which said aromatic means is forced out; means for mounting said squeezable bag in said housing; and tray means mounted in said housing directly below said outlet means so that when said aromatic means is forced out of said squeezable bag, said aromatic means drops onto said tray means where said aromatic means evaporated to give off a scent to awaken a sleeper; said housing further having an opening formed therein adjacent said tray means through which said evaporated aromatic means exits.

2. The scent-awake alarm clock according to claim 1, wherein said outlet means comprises a hollow needle having a first end projecting into the interior of said squeezable bag adjacent the bottom of said bag, and a second end remote from said first end and outside of said squeezable bag, said hollow needle being mounted in said means for mounting said squeezable bag, said aromatic means exiting through said hollow needle via the first end thereof when said plunger means impinge downwardly on the upper surface of said bag.

3. The scent-awake alarm clock according to claim 1, further comprising a fan means for stirring the air in said housing when said aromatic means is dispensed in said tray; and said means for activating said actuating means comprises means for intermittently operating said actuating means and said fan means so that said aromatic means is dispensed at intervals.

4. The scent-awake alarm clock according to claim 1, further comprising a fan means for speeding up the evaporation of said aromatic means in said tray means and said housing comprising an opening formed therein adjacent said tray means so that said evaporated aromatic means may exit therethrough.

5. The scent-awake alarm clock according to claim 1, wherein said tray means is mounted in said housing below said means for storing and dispensing, said tray means having a layer of absorbing material thereon, to absorb the dispensed aromatic means dropped thereon.

6. A scent-awake alarm clock for awakening a sleeper through the sense of smell comprising, a housing; aromatic means in said housing for giving off a scent when dispensed; means for storing and dispensing said aromatic means in said housing; actuating means operably connected to said means for storing and dispensing, said actuating means selectively causing said aromatic means to be dispensed from said means for storing and dispensing; and timing means for activating said actuating means at a predetermined time, said aromatic means comprising a liquid stored in said means for storing and dispensing; said means for storing and dispensing comprising a container, and said actuating means comprising a solenoid electrically connected to said means for activating, and a lever arm pivoted at one end thereof to said housing, the other end of said lever arm being connected to the plunger of said solenoid for movement thereby, said lever arm operating said means for storing and dispensing said aromatic means to thereby dispense said aromatic means, wherein said actuating means further comprises a connecting lever having a first end pivotally connected to said lever arm between one end and said other end thereof, and a second end remote from said first end and positioned adjacent said container, and a flat plate having a first end pivotally connected to said second end of said connecting lever, and a second free end, said connecting lever and said flat plate being moveable along with the movement of said lever arm, said container comprising a U-shaped tube having a first opening positioned near the bottom of said container, said flat plate alternately closing off and opening said first opening to the ambient air, and a second opening positioned within said container at a higher vertical level than said first opening, said second opening being positioned in said container above the liquid lever thereof so that when said flat plate is moved away to expose said first opening to the air, the vacuum in said container is broken and the liquid level is forced downwardly; said container further having an outlet tube through which the aromatic means exists upon the supply of air to the interior of the container; and tray means mounted directly below said outlet means on which said aromatic means drops to thus be evaporated.

7. The scent-awake alarm clock according to claim 6, wherein said housing has an opening formed therein adjacent said tray means so that said evaporated aromatic means may exit therethrough; and fan means for blowing air onto said tray means to thus speed up the rate of evaporation; said activating means comprising means for intermittently operating said solenoid and said fan means.

* * * * *